United States Patent

George et al.

[11] Patent Number: 5,192,763
[45] Date of Patent: Mar. 9, 1993

[54] [(1-ARYLPYRROLIDIN-2-YL)METHYL]PIPERAZINE DERIVATIVES, THEIR PREPARATION AND THEIR APPLICATION IN THERAPEUTICS

[75] Inventors: Pascal George, St. Arnoult en Yvelines; Jacques Menin, Vitry sur Seine; Jean-Pierre Merly, Sceaux; Dennis Bigg, Castres; Daniel Obitz, Antony; Michel Peynot, L'Hay-les-Roses; Corinne Veronique, Villejuif, all of France

[73] Assignee: Synthelabo, Paris, France

[21] Appl. No.: 710,711

[22] Filed: Jun. 6, 1991

[30] Foreign Application Priority Data

Jun. 7, 1990 [FR] France ................. 90 07067

[51] Int. Cl.$^5$ ................. H61K 31/495; C07D 403/06
[52] U.S. Cl. ..................... 514/252; 544/225; 544/372; 548/572
[58] Field of Search ........... 544/372; 514/252

[56] References Cited

U.S. PATENT DOCUMENTS 3,250,771  5/1966  Leonard et al. ............ 544/372
5,063,242  11/1991  Horwell et al. ............ 514/414

OTHER PUBLICATIONS

Monnet et al, *J. Pharm. Exp. Ther.* 261, p. 123 (1992).
Greenamyre, *Arch. Neurol.* 43, p. 1058 (1986).
Olney, *Biol. Psychiatry* 26, p. 505 (1989).

Primary Examiner—Mukund J. Shah
Assistant Examiner—E. Bernhardt
Attorney, Agent, or Firm—Jacobson, Price, Holman & Stern

[57] ABSTRACT

[(1-Arylpyrrolidin-2-yl)methyl]piperazine compounds corresponding to the formula

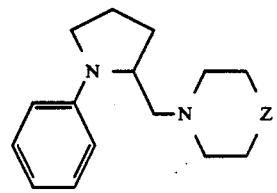

(I)

in which Z denotes a group of formula $N-R_1$ in which $R_1$ is either a hydrogen atom or a $C_{1-3}$ alkyl group or a group of formula $Ar-C_nH_{2n}$ in which n denotes 0, 1 or 2 and Ar denotes a phenyl group optionally substituted by one or more halogen atoms and/or $C_{1-3}$ alkyl or $C_{1-3}$ alkoxy radicals, or a group of formula $COR_2$ in which $R_2$ denotes the $CH_3$, $C_6H_5$, $CH_2C_6H_5$ or $OC_2H_5$ group and their salts of addition to pharmaceutically acceptable acids. The compounds are useful for the treatment of neurological disorders.

8 Claims, No Drawings

[(1-ARYLPYRROLIDIN-2-YL)METHYL]PIPERAZINE DERIVATIVES, THEIR PREPARATION AND THEIR APPLICATION IN THERAPEUTICS

The present invention relates to [(1-arylpyrrolidin-2-yl) methyl]piperazine derivatives, their preparation and their application in therapeutics.

The compounds of the invention are [(1-arylpyrrolidin-2-yl)methyl]piperazine derivatives in the form of racemates or enantiomers, which derivatives, are compounds of formula

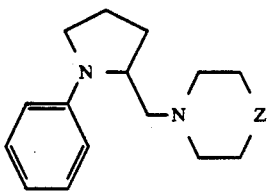
(I)

in which Z represents a group of formula -N-R$_1$ in which R$_1$ is hydrogen, C$_{1-3}$ alkyl a group of formula Ar—C$_n$H$_{2n}$— in which n is 0, 1 or 2 and Ar represents a phenyl group optionally substituted by one or more halogen atoms and/or at least one C$_{1-3}$ alkyl or C$_{1-3}$ alkoxy group, or a group of formula —COR$_2$ in which R$_2$ represents —CH$_3$,—C$_6$H$_5$,—CH$_2$C$_6$H$_5$ or —OC$_2$H$_5$, or their salts of addition to pharmaceutically acceptable acids.

The preferred derivatives of the invention are those in which Z denotes an —N—(CH$_2$)$_2$—Ar group where Ar is as defined above. More preferably Ar is a phenyl group optionally substituted by one or more fluorine or chlorine atoms and/or by one or more methyl or methoxy groups.

Preferred salts are hemifumarate, difumarate, dihydrochloride or maleate addition salts.

The derivatives of the invention can be prepared according to the reaction scheme given in the appendix.

The derivatives of the invention may be prepared by either (a) reacting an ester derived from the proline of formula (II)

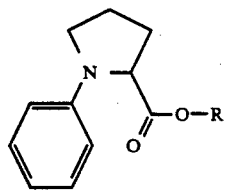
(II)

at a temperature of from 80° to 110° C., with a trimethylaluminium-amine complex of formula (III)

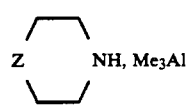
(III)

wherein Z is as defined in claim 1 to obtain an amide of formula (IV)

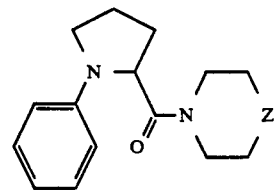
(IV)

or (b) reacting proline (V)

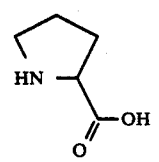
(V)

with a halide C$_6$H$_5$Hal in the presence either of a Cu++ salt or of metallic copper at a temperature of from 10020 to 150° C., to obtain an acid of formula (VI)

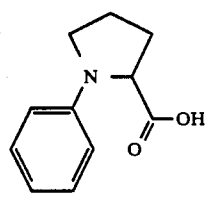
(VI)

and converting the acid (VI) into said amide (IV) by treatment with carbonyldiimidazole at a temperature of from 20° to 40° C., to form an intermediate imidazolide which is treated in situ with an amine of formula

in which Z is as defined in claim 1; reducing the amide of formula (IV)

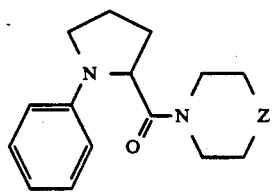
(IV)

to a compound of formula I with lithium aluminium hydride at a temperature of from 20° to 50° C. and, if desired, forming an acid addition salt of the compound of formula (I) in manner known per se.

Preferably the ester (II) is reacted with the trimethylaluminium amine complex (III) in an inert solvent such as toluene. The Cu++ salt is preferably CuO and the proline (V) may be reacted with the halide C$_6$H$_5$Hal in the presence of a base such as K$_2$C0$_3$. The reaction between the proline (V) and the halide C$_6$H$_5$Hal may be carried out in an aprotic solvent such as dimethylformamide or N-methylpyrrolidone according to the condition described in the Ullmann reaction (Synthesis 9(1974). The acid (VI) may be treated with carbonyldiimidazole in a solvent such as tetrahydrofuran (THF) or methylene chloride and the amide (IV) is preferably reduced with lithium aluminium hydride in an ether solvent such as ether or THF.

The esters of formula (II) can be prepared according to the method described in Khim. Farm. Zh. 1970,4 (9), pages 27-31 (CA 74-012920).

The compounds of formula (I) in which Z=NH can also be obtained 1) either by debenzylation of the compounds of formula (IV) in which $Z=N-CH_2-C_6H_5$ with hydrogen in the presence of a catalyst such as palladium absorbed on an inert support, at a temperature ranging from 20° to 60° C., in a protic solvent such as ethanol or acetic acid, at a pressure of 100 to 400 kPa, followed by a reduction of the compound of formula (IV) in which Z=NH, which is thus obtained, with $LiAlH_4$ in an ether solvent such as ether or THF, at a temperature ranging from 20° to 50° C.; 2) or by reaction of the compounds of formula (IV) in which $Z=N-CH_2-C_6H_5$ with an alkyl chloroformate, more particularly ethyl chloroformate, in a chlorinated solvent such as $CH_2Cl_2$, at a temperature ranging from 0° to 20° C., followed by saponification of the compounds of formula (IV) in which $Z=NCO_2Et$ with sodium hydroxide in ethanol, at a temperature ranging from 20° to 80° C. and by reduction of the compounds of formula (IV) in which Z=NH with $LiAlH_4$ under the same conditions as above.

The compounds of formula (I) in which Z denotes a group of formula $NCOR_2$ can also be obtained by reaction of the compounds of formula (I) in which Z is NH with a reactant of formula $R_2COHal$ in which $R_2$ is defined as above and Hal denotes a halogen atom, in an inert solvent such as $CH_2Cl_2$, toluene or DMF, optionally in the presence of an inorganic base such as $K_2CO_3$ or an organic one such as triethylamine (TEA), at a temperature ranging from 20° to 100° C.

The racemates can be obtained by starting with (D,L)-proline. The pure enantiomers can be obtained either by starting with L(−)-proline or with (D)(+)-proline, or by resolving the racemic mixture with a resolving agent such as a optically active acid.

The following examples illustrate the preparation of the compounds according to the invention.

Analyses and IR and NMR spectra confirm the structure of the compounds.

EXAMPLE 1

[1-(Benzyl)-4-(1-phenylpyrrolidin-2-yl)methyl]-piperazine and its dihydrochloride 1.1.
[1 TM (Benzyl)-4-(1-phenylpyrrolidin-2-yl)carbonyl]-piperazine A solution of 9.55 g (0.054 mol) of 1-benzylpiperazine in 20 cm³ of toluene is added dropwise, under argon, at 0–5° C., to a solution of 3.8 g (0.0526 mol) of trimethylaluminium (22 cm³ of a 25% solution in hexane) in 40 cm³ of toluene. The mixture is then heated to 50° C. and 7.43 g (0.0339 mol) of ethyl 1-phenylpyrrolidine-2-carboxylate in 40 cm³ of toluene are added slowly. At the end of the addition the mixture is heated to 80–90° C., hexane is distilled off and the mixture is refluxed for 3 hours. A clear, orange-coloured solution is obtained which is cooled and hydrolysed with 50 cm³ of water. It is filtered and the insoluble material is rinsed with ethyl acetate, and the organic phase is separated off, washed with water and dried. The solution is concentrated at reduced pressure; a yellow oil is obtained which is taken up in a cyclohexane/toluene (1/1) mixture. The solution is filtered and ground and a white solid is obtained. W=10.3 g. M=99-100.5° C.

1.2.
[1-(Benzyl)-4-(1-phenylpyrrolidin-2-yl)methyl]-piperazine and its dihydrochloride 1.65 g (0.0434 mol) of $LiAlH_4$ in 75 cm³ of dry THF are introduced under argon into a 1—1 three-necked round bottom flask, and 10.1 g (0.0289 mol) of the compound obtained in 1.1. are then added at 0-5° C. in 200 cm³ of dry THF. The materials are left in contact for 30 min and are then refluxed for 6 hours. The mixture is treated with 15 cm³ of 6.5% NaOH, with cooling. The solution obtained is filtered and the insoluble material is rinsed with THF. The organic phases are combined, dried and concentrated at reduced pressure. A yellow oil is obtained. The hydrochloride of the compound is prepared by reacting 9.7 g (0.0289 mol) of base and 580 cm³ of HCl in isopropanol (0.1 m/1). The solution is concentrated completely, AcOEt is added and the product is ground. The white solid is recrystallised from an isopropanol/MeOH (1/1) mixture.

W=10.8 g. M=249-251° C. Yield=91.5%.

EXAMPLE 2

1-[(1-Phenylpyrrolidin-2-yl)methyl]piperazine and its hemifumarate 2.1. 1-[(1-Phenylpyrrolidin-2-yl)carbonyl]piperazine Synthesis Route 1

3.49 g (0.01 mol) of the compound of Example 1.1, dissolved in 100 ml of ethanol, are reacted, in the presence of 0.5 g of 10% palladium/C and of 10 ml of 1N hydrochloric acid, with gaseous hydrogen at a pressure of 4 atm for 5 h at a temperature of 20 to 25° C. At the end of reaction the catalyst is filtered off and the filtrate is concentrated at reduced pressure. The residue is treated with an excess of aqueous ammonia and is extracted with $CH_2Cl_2$. The organic phase is dried over $Na_2SO_4$ and is concentrated. 2.5 g, i.e. 96%, of white solid are obtained. M=128-130° C.

Synthesis Route 2

Ethyl 4-[(1-phenylpyrrolidin-2-yl)carbonyl]piperazine-1-carboxylate 53.0 g (0.152 mol) of the compound of Example 1.1 are introduced under argon into 500 cm³ of $CH_2Cl_2$ and 18.2 g (0.168 mol) of ethyl chloroformate are added at room temperature. The mixture is left stirred for 72 hours at room temperature.

The solution is concentrated, the residue is taken up with $CH_2Cl_2$, is washed with sodium water and then with water, and is dried and concentrated. The solid obtained is recrystallised from a cyclohexane/ toluene (4/1) mixture. W=42.7 g. Yield=84.9%. M=139.5-141.5° C.

1-[(1-Phenylpyrrolidin-2-yl)carbonyl]piperazine 46.1 g (0.139 mol) of the compound obtained above and 300 cm³ of ethanol are introduced under argon into a 1-1 three-necked round bottom flask. The mixture is heated to boiling and 85 cm³ (0.834 mol) of a sodium hydroxide solution are added. The mixture is boiled for 18 hours. 700 cm³ of water are added and the mixture is extracted with CH₂Cl₂. The organic phase is dried over MgSO₄. It is concentrated at reduced pressure and a white solid is obtained, which is recrystallised from toluene.

W=31.6 g. Yield=87.5%. M=128-130° C.

2.2. 1-[(1-Phenylpyrrolidin-2-yl)methyl]piperazine and its hemifumarate 5.84 g (0.154 mol) of LiAlH₄ in 600 cm³ of dry THF are introduced under argon into a 1-1 three-necked round bottom flask and 2666 g (0.103 mol) of amide 2.1 are then added at the temperature of 0–5° C. The mixture is left in contact for 30 min and is then refluxed for 2 hours. It is then treated with 70 cm³ of 6 5% NaOH, with cooling. The suspension obtained is filtered and the insoluble material is washed with ethyl acetate. The filtrate is dried over MgSO₄ and concentrated at reduced pressure. A yellow oil is obtained, w=23.5 g, yield: 93.3%.

The hemifumarate of this compound is prepared by reacting 5.0 g (0.0204 mol) of base in 50 cm³ of ethanol and 1.19 g (0.0102 mol) of fumaric acid in 100 cm³ of ethanol. The solution is concentrated at reduced pressure and the solid residue is recrystallised from methanol.

W=1.3 g. Yield 22%. M=179.5-181° C.

EXAMPLE 3

1-(2-Phenylethyl)-4-[(1-phenylpyrrolidin-2-yl)methyl]-piperazine and its dihydrochloride 3.1.
1-(2-Phenylethyl)-4-[(1-phenylpyrrolidin-2-yl)carbonyl]piperazine A solution of 10.3 g (0.0542 mol) of 1-(2)-phenylethyl)piperazine in 20 cm³ of toluene is added dropwise, under argon, at 0–5° C., to a solution of 3.8 g (0.0526 mol) of trimethylaluminium (22 cm³ of a 25% solution in hexane) in 40 cm³ of toluene.

The mixture is heated to 50° C. and 7.43 g (0.0339 mol) of ethyl 1-phenylpyrrolidine-2 TM carboxylate in 40 cm³ of toluene are added dropwise. At the end of addition the mixture is heated to 80° C., hexane is distilled off and the mixture is refluxed for 3 hours. The solution is cooled and hydrolysed with 50 cm³ of water. The solution is filtered, the insoluble material is washed with ethyl acetate, the solution is separated, washed with water, dried and concentrated. The oil is taken up in hot cyclohexane. The residue is filtered and ground. A white solid is obtained.

W=11.4 g. Yield=92.7%. M=123-124.5° C.

3.2.
1-(2-Phenylethyl) TM 4-[(1-phenylpyrrolidin-2-yl)methyl]piperazine and its hydrochloride 1.25 g (0.0330 mol) of LiAlH₄ in 50 cm³ of dry THF are introduced under argon into a 500-cm³ three-necked round bottom flask and 8.0 g (0.0220 mol) of the compound 3.1 in 100 cm³ of dry THF are then added at 0–5° C. The mixture is left in contact for 30 min and is then refluxed for 7.5 hours. The solution is treated with 10 cm³ of 6.5% NaOH, with cooling.

The suspension is filtered, the insoluble material is rinsed with THF, and the solution is dried and concentrated. A yellow oil is obtained.

The dihydrochloride is prepared by reacting 6.6 g (0.0189 mol) of base 3.2 and 380 cm³ of HCl in isopropanol (0.1 m/l). The solution is concentrated to ⅔. A white solid is obtained, which is filtered off and recrystallised from an isopropanol/MeOH (⅓) mixture.

W=6.9 g. Yield=74.2%. M=272-275° C.

EXAMPLE 4

1-(Phenylcarbonyl)-4-[(1-phenylpyrrolidin-2-yl)methyl]-piperazine and its hydrochloride 5.0 g (0.0204 mol) of 1-[(1-phenylpyrrolidin-2-yl)methyl]piperazine in 75 cm³ of CH₂Cl₂ are introduced under argon into a 500-cm³ three-necked round bottom flask. 7.2 g (0.0714 mol) of triethylamine are added. 3.0 g (0.0214 mol) of benzoyl chloride in 40 cm³ of CH₂Cl₂ are added to the solution. The mixture is stirred at room temperature for 1.5 hours. The solution is treated with 200 cm³ of water, the organic phase is separated off, is washed with water, is dried and is concentrated at reduced pressure. An oil is obtained, which is chromatographed on a silica column (eluent 99/1 CH₂Cl₂/methanol).

The hydrochloride is prepared by reacting 3.1 g (0.00887 mol) of base and 89 cm³ of HCl in isopropanol (0.1 m/l).

The solution is evaporated down completely. A solid is obtained, which is recrystallised twice from an isopropanol/MeOH (4/1) mixture. M=227-230° C. Yield 32.9%.

EXAMPLE 5

(S)-1-(2-Phenylethyl)-4-[(1-phenylpyrrolidin-2-yl)methyl]piperazine and its dihydrochloride 5.1. (S)(−)-1-Phenylpyrrolidine-2-carboxylic acid Into a 2-1 three-necked round bottom flask are introduced 158 g (1.37 mol) of (L)(−)proline, 220 g (1.40 mol) of bromobenzene, 194 g (1.40 mol) of K₂CO₃ and 10 g of CuO in 450 ml of DMF. The mixture is heated to reflux temperature for 37 hours. It is allowed to cool, 1 l of water is added, the mixture is filtered through celite, the impurities are extracted with CH₂Cl₂, and the mixture is filtered again and acidified with dilute HCl to pH 4.0.

It is extracted with CH₂Cl₂, washed with water, dried and the solvent is evaporated off at reduced pressure. A white solid is obtained. M=80-81° C.

5.2.
(S)(−)-1-(2-Phenylethyl)-4-[(1-phenylpyrrolidin-2-yl)carbonyl]piperazine 16.2 g (0.1 mol) of carbonyldiimidazole are added to a solution of 14.2 g of acid prepared in 5.1 in 100 ml of THF and are left stirred for 2 hours at 20° C. and then for 12 h at 40° C. 14 g (0.074 mol) of 1-(2-phenylethyl)-piperazine are then added and are left stirred overnight at 20° C. and then for 3 h at 50° C. The mixture is evaporated to dryness, the residue is taken up with water containing sodium bicarbonate and is extracted with CH₂Cl₂ and the organic phase is dried and is concentrated at reduced pressure. A brown oil is obtained, which is purified by chromatography on a silica column (eluent: 95/5 CH₂Cl₂/ethyl acetate, then 95/5 CH₂Cl₂/methanol).

10 g of crude product are recovered and are dissolved in ether and reprecipitated with pentane. 8 g of white solid are obtained (i.e. 30% yield), which is employed in this form for the next stage.

5.3.

Some compounds of the invention, prepared by way of examples, are shown in the table which follows.

TABLE

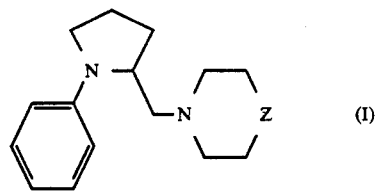

(I)

| No. | Z | Salt | M (°C.) | $[\alpha]_D$ (°) |
|---|---|---|---|---|
| 1 | N—H | ½ fum. | 179.5–181 | d, 1 |
| 2 | N—CH$_3$ | HCl | 190.5–192 | d, 1 |
| 3 | N—C$_6$H$_5$ | HCl | 248–252 | d, 1 |
| 4 | N—CH$_2$—C$_6$H$_5$ | 2 HCl | 249–251 | d, 1 |
| 5 | N—CH$_2$—(4-Cl—C$_6$H$_4$) | 2 HCl | 249–251.5 | d, 1 |
| 6 | N—(CH$_2$)$_2$—C$_6$H$_5$ | 2 HCl | 272–275 | d, 1 |
| 7 | N—CH(CH$_3$)—C$_6$H$_5$ | 2 fum. | 190–193 | d, 1 |
| 8 | N—COCH$_3$ | HCl | 250.5–253.5 | d, 1 |
| 9 | N—CO$_2$C$_2$H$_5$ | HCl | 226–228 | d, 1 |
| 10 | N—COC$_6$H$_5$ | HCl | 227–230 | d, 1 |
| 11 | N—(CH$_2$)$_2$—C$_6$H$_5$ | 2 HCl | 266–267 | −15 (c = 0.2, EtOH) |
| 12 | N—(CH$_2$)$_2$—(4-CH$_3$O—C$_6$H$_4$) | 2 HCl | 258–260 | d, 1 |
| 13 | N—(CH$_2$)$_2$—(4-Cl—C$_6$H$_4$) | 2 HCl | 247–249 | d, 1 |
| 14 | N—(CH$_2$)$_2$—(3-CH$_3$O—C$_6$H$_4$) | 2 HCl | 235–237 | d, 1 |
| 15 | N—(CH$_2$)$_2$—(4-F—C$_6$H$_4$) | 2 HCl | 250–253 | d, 1 |
| 16 | N—(CH$_2$)$_2$—(2-CH$_3$O—C$_6$H$_4$) | 2 HCl | 235–237 | −16.7 (c = 1, DMF) |
| 17 | N—(CH$_2$)$_2$—(4-CH$_3$—C$_6$H$_4$) | 2 HCl | 255–257 | −34.5 (c = 0.2, 95% EtOH) |
| 18 | N—(CH$_2$)$_2$—(3-CH$_3$—C$_6$H$_4$) | 2 HCl | 250 (decomp.) | −19.2 (c = 1, 95% EtOH) |
| 19 | N—(CH$_2$)$_2$—(2-CH$_3$—C$_6$H$_4$) | 2 HCl | 250 (decomp.) | −18.4 (c = 1, 95% EtOH) |
| 20 | N—(CH$_2$)$_2$—(2-Cl—C$_6$H$_4$) | 2 HCl | 241–243 | −12.5 (c = 1, 95% EtOH) |
| 21 | N—(CH$_2$)$_2$—(3-Cl—C$_6$H$_4$) | 2 HCl | 245–248 | −21 (c = 0.5, 95% EtOH) |
| 22 | N—(CH$_2$)$_2$—(3,4-diCH$_3$O—C$_6$H$_3$) | 2 fum. | 204–206 | −28 (c = 0.1, 95% EtOH) |
| 23 | N—(CH$_2$)$_2$—(3,4-diCl—C$_6$H$_3$) | 2 mal. | 208–210 | −25 (c = 0.1, 95% EtOH) |
| 24 | N—CO—CH$_2$—C$_6$H$_5$ | HCl | 220–222 | d, 1 |
| 25 | N—(CH$_2$)$_2$—(2-F—C$_6$H$_4$) | 2 HCl | 247–250 | −29 (c = 0.1, 95% EtOH) |
| 26 | N—(CH$_2$)$_2$—(3-F—C$_6$H$_4$) | 2 HCl | 246–249 | −33 (c = 0.1 95% EtOH) |
| 27 | N—(CH$_2$)$_2$—C$_6$H$_5$ | 2 HCl | 256–258 | +15.2 (c = 0.2, EtOH) |

½ fum. = hemifumarate
2 fum. = difumarate
2 HCl = dihydrochloride
2 mal. = maleate (S)(−)-1-(2-Phenylethyl)-4-[(1-phenylpyrrolidin-2-yl)methyl] piperazine and its dihydrochloride A solution of 6.9 g (0.019 mol) of amide prepared according to 5.2, in 100 ml of dry THF, is added to a suspension of 1.07 g (0.028 mol) of LiAlH$_4$ in 100 ml of dry THF. The mixture is refluxed for 3 h and is then cooled and hydrolysed with 1N NaOH. A solid forms, the organic phase is separated off, diluted with CH$_2$Cl$_2$ and dried. The solvents are evaporated off at reduced pressure. 7 g of oil are obtained, which are purified by chromatography on a silica column (eluent: 97/3 CH$_2$Cl$_2$/ethyl acetate, then 95/5 CH$_2$Cl$_2$/methanol). 6 g of oil are isolated.

The dihydrochloride is prepared by means of 5.43 g (0.0155 mol) of base and 311 ml of 0.1 N hydrochloric acid in 2-propanol; the salt is recrystallised from methanol. 5.2 g of dihydrochloride are obtained. M=266–267° C., $[\alpha]_D$=−15° (c=0.2, ethanol).

The compounds of the invention have been the subject of a series of pharmacological tests which demonstrated their advantage as substances with therapeutic activities.

Antiischaemic Activity

1. The cerebral antiischaemic properties of the compounds of the invention were evaluated on the overall cerebral ischaemia test in the mouse.

The overall cerebral ischaemia is induced in the mouse after a cardiac arrest produced by injecting a saturated MgCl$_2$ solution into the caudal vein. Preliminary studies showed that the drop in arterial pressure is similar in all the animals and that it is practically nil after 6.3±0.8 s. The cardiac arrest is sufficiently sudden for the magnesium chloride not to reach the cerebrovascular capillary bed.

The "survival time" is the time which separates the injection of magnesium chloride from the last inspiratory movement. The complete disappearance of cerebral energy reserves or, more precisely, the loss of the autorhythmicity of the cerebral respiratory centres is reflected in an arrest of the thoracic movements. This respiratory arrest takes place approximately 19 s after the injection of magnesium chloride.

The survival time is measured 10 minutes after an intraperitoneal injection or 30 minutes after the oral administration of the compound t be tested. The difference between the survival time of the treated animals and the survival time of the control animals is plotted on a graph as a function of the logarithm of the dose (expressed as base). The $ED_{3''}$ dose is the dose which increases the survival time of the treated animals by 3 seconds. This value is reproducible and is always statistically significant.

The $ED_{3''}$ doses of the compounds of the invention lie between 10 and 200 mg/kg by intraperitoneal route and/or by oral route.

2. The neuroprotective activity of the compounds of the invention was shown in a focal ischaemia model by ligature of the mean cerebral artery in the mouse, by a method similar to that described in Brain Research, 522, (1990), 290–307. Six days after occlusion of the mean cerebral artery by electro-coagulation under anaesthesia with halothane, the mice are anaesthetised again and the ipsilateral cerebral cortex at the occlusion is removed. Afte homogenisation of the tissue, the extent of the cerebral infarctus is evaluated by measuring the increase in the density of the peripheral benzodiazepinic sites ($\omega_3$) with the aid of the compound [$^3H$]-PK 11195 from New England Nuclear. The treatments are administered curatively at times of 5 min, 3 h, 6 h, 18 h and 24 h, by intraperitoneal route.

With the compounds of the invention the reduction in the size of the lesion ranges from 40% to 70% (for a dose ranging from 0.1 to 30 mg/kg).

Anticonvulsive Activity

The compounds of the invention inhibit the tonic convulsions induced in the mouse by a supramaximal electric shock. The compounds being ddministered by intraperitoneal route 30 minutes, or by oral route 60 minutes, before the application of an electric shock to the cornea (10 mA, 50 Hz for 0.5 s), the $DA_{50}$, doses which inhibit the convulsive effects of the electric shock in 50% of the animals, are determined graphically.

For the compounds of the invention the $DA_{50}$ values lie between 10 and 100 mg/kg by intraperitonea route.

Specific Binding to the Sigma Sites

The compounds were subjected to a test of inhibition of the binding of [$^3H$]-(+)-3-(3-hydroxyphenyl)-N-(1-propyl)piperidine, or [$^3H$]-(+)-3-PPP, to the $\sigma$ receptors of the rat brain, according to the protocol described by Largent et al. in J. Pharmacol. Exp. Ther., 238, 739–748 (1986). Male Sprague-Dawley rats of 150 to 200 g are sacrificed and their cerebral cortex is homogenised in 25 volumes of iced Tris-HCl buffer at a concentration of 50 mM (pH=7.4 at 25° C.) by means of an Ultra-Turrax TM apparatus. The mixture is washed twice by being centrifuged for 10 min at 45,000 g and by resuspending the pellet in fresh buffer. The washed pellet is diluted in 20 volumes of Tris buffer (HCl at a concentration of 50 mM, pH=8.0 at 22° C.), and 75-$\mu$l aliquot fractions are incubated in a final volume of 250 $\mu$l containing 2 nM of [:H]-(+)-3PPP (specific activity: 90 Ci/mmol, from New England Nuclear), for 90 min at 25° C. in the absence or in the presence of competing substances.

After incubation, the membranes are recovered by filtration on Whatman GF/B TM filters treated with polyethyleneimine at a concentration of 0.05% by means of a Skatron Cell Harvester TM apparatus, and are washed with approximately 2.5 ml of iced Tris-HCl buffer (pH=7.7 at 0° C.).

The nonspecific binding is determined with 1 $\mu$M haloperidol, the data are analysed by the usual methods and the concentration $IC_{50}$, which inhibits the binding of [$^3H$]-(+)-3PPP by 50% is calculated for each compound.

The $IC_{50}$ values (in $\mu$M) of the compounds of the invention lie between 0.001 and 0.2 $\mu$M.

Lastly, the acute toxicity of the compounds of the invention was evaluated in the mouse. The lethal doses $LD_{50}$, doses which cause 50% mortality in the animals, lie between 30 and 300 mg/kg by intraperitoneal route, and between 100 and 1000 mg/kg by oral route.

The results of the tests show that, in vitro, the compounds displace [$^3H$]-(+) TM 3-PPP from its cerebral binding sites and consequently exhibit an affinity for the sigma sites.

In vivo, they have antiischaemic and anticonvulsive properties.

They can be employed for the treatment or the protection against cerebral ischaemias of diverse origins, such as hypoglycaemic and hypoxic ischaemias and, in general, in the treatment of metabolic encephalopathies, in the protection against neuronal degenerescence and aminoacidopathy involving a disorder of the neuronal function and in the treatment of neurological disorders. They can also be employed for the treatment of neurological disorders such as convulsive states in general, in particular epilepsy and spasticity, stress and anxiety states, psychotic states in general, and schizophrenia.

For this purpose they may be presented in any forms which are appropriate to their administration by oral or parenteral route, in combination with any suitable excipients, and can be in doses to permit a daily posology of 1 to 1000 mg.

APPENDIX

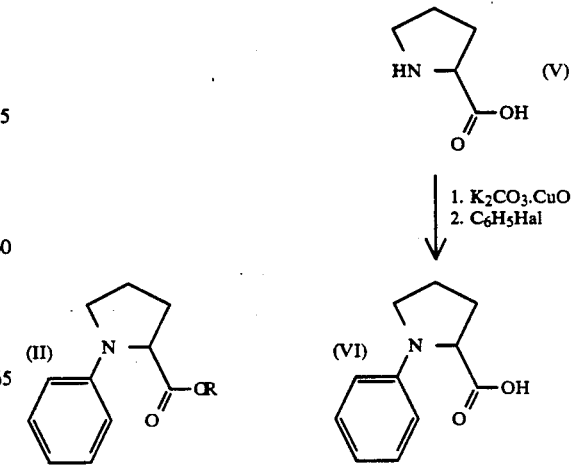

APPENDIX

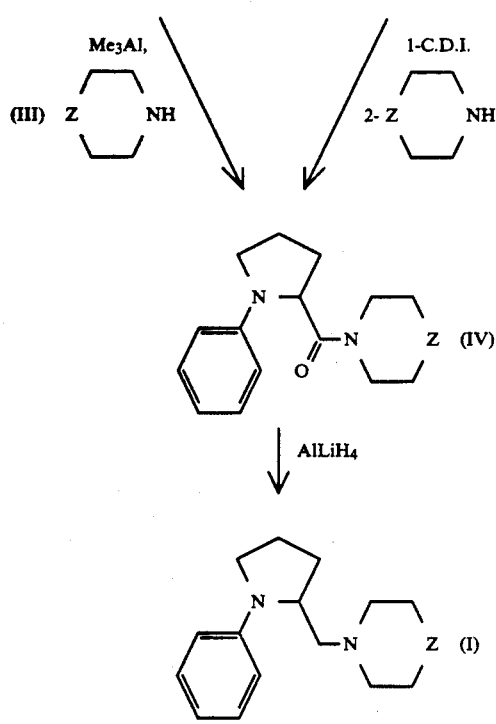

We claim:

1. piperazine compounds in the form of racemates or enantiomers, which compounds correspond to the formula:

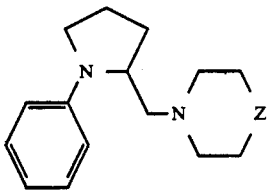

in which Z represents a group of formula -N-$R_1$ in which $R_1$ is hydrogen, $C_{1-3}$ alkyl, a group of formula Ar—$C_nH_{2n}$— in which n is 0, 1 or 2 and Ar represents a phenyl group optionally substituted by one or more halogen atoms and/or $C_{1-3}$ alkyl or $C_{1-3}$ alkyl or $C_{1-3}$ alkoxy group, or a group of formula —$COR_2$ in which $R_2$ represents —$CH_3$, —$C_6H_5$, —$CH_2C_6H_5$ or —$OC_2H_5$, or their pharmaceutically acceptable acid addition salts.

2. Compounds according to calim 1, in which Z denotes the —N—$(CH_2)_2$—Ar group.

3. Compounds according to claim 2, wherein Ar denotes a phenyl group optionally substituted by one or more fluorine or chlorine atoms and/or by one or more methyl or methoxy groups.

4. Compounds according to claim 1, which are hemifumarate, difumarate, dihydrochloride or maleate addition salts.

5. A pharmaceutical composition useful for treating a cerebral ischaemia or a convulsive state, which comprises an effective amount of a compound as claimed in claim 1 and a pharmaceutically acceptable excipient.

6. A method of treating a cerebral ischaemia or a convulsive state, which comprises administering to a thus-afflicted patient an effective amount of a compound as claimed in claim 1.

7. A method according to claim 6, wherein the cerebral ischaemia is a hypoglycemic or hypoxic ischaemia.

8. A method according to claim 6, wherein the convulsive state is epilepsy or spasticity.

* * * * *